United States Patent [19]
Silberstein et al.

[11] Patent Number: 5,977,145
[45] Date of Patent: Nov. 2, 1999

[54] METHOD OF TREATING MIGRAINE

[75] Inventors: Stephen D. Silberstein, Philadelphia; William B. Young, Erdenheim, both of Pa.

[73] Assignee: Taylor Pharmaceuticals, Buffalo Grove, Ill.

[21] Appl. No.: 09/022,312

[22] Filed: Feb. 12, 1998

[51] Int. Cl.$^6$ .................................... A61K 31/44

[52] U.S. Cl. ............................................. 514/338

[58] Field of Search ............................... 514/338

[56] References Cited

PUBLICATIONS

Wang, et al. *Droperidol Treatment of Status Migrainosus and Refractory Migraine*, Headache. Jun., 1997, pp. 377–382.

Wang, et al. *Droperidol Treatment of Acute Refractory Migraine and Status Migrainosus*, Headache, Apr. 1996, p. 280.

John F. Rothrock, MD., *Treatment of Acute Migraine with Intravenous Droperidol*, Apr. 1997, pp. 256–257.

*Primary Examiner*—Phyllis G. Spivack
*Attorney, Agent, or Firm*—Leydig, Voit & Mayer, Ltd.

[57] ABSTRACT

Intravenous or intramuscular injection of droperidol is disclosed to treat migraine episodes.

6 Claims, No Drawings

METHOD OF TREATING MIGRAINE

FIELD OF THE INVENTION

This invention relates to the field of migraine treatment.

BACKGROUND OF THE INVENTION

The prevalence of migraine is said to be approximately 6% of the male population and 18% of the female population. Treatment for many patients having the occasional migraine usually involves simple analgesics, non-steroidal anti-inflammatory agents, or specific agents such as ergotamines or triptans. Approximately 10% of migraine sufferers have three or more attacks per month and warrant prophylactic treatment. Preventative agents such as beta-blockers, tricyclic antidepressants and divalproex sodium can reduce but not eliminate migraine attacks in some patents. Thus, there remains a need for migraine specific medications such as sumatriptan. In the remaining population of migraine sufferers, and in those with intolerable side-effects from available drugs, there is a lack of conventional pharmaceutical preparations that exhibit therapeutic effect, without severe side-effects.

Droperidol presently is marketed by Akorn, Inc. under the trademark Inapsine, as an injectable formulation used in anesthesia for preoperative surgery. It has never been approved for use in the treatment or management of migraine attacks.

Preliminary results regarding a limited, uncontrolled, non-blinded, use of droperidol to treat migraine attacks were published in *Headache*, April 1996, p.280. That publication is authored by the inventors of the present invention. Although the article reports on apparently encouraging results in treating migraine attacks with droperidol, no definitive conclusions can be reached from the results reported in that article.

SUMMARY OF THE INVENTION

In accordance with the present invention droperidol is administered, either intravenously ("I.V.") or intramuscularly ("I.M."), to a patient during a migraine attack, in an amount that is effective to treat symptoms of migraine. Droperidol may be used without pretreatment or in conjunction with other migraine therapies.

DETAILED DESCRIPTION OF THE PREFERRED EMBODIMENTS

As indicated, patients that are suffering from a migraine episode are treated with droperidol, administered either I.V. or I.M. The droperidol is typically administered in dosages of 2.5 mg every 15 to 45 minutes until headache symptoms subside. Most typically the administration will occur about every thirty minutes until the symptoms subside. The maximum dosage of droperidol administered to a patient at a single session usually will be 7.5 mg, although it may on occasion be as high as 10 mg.

The patients receiving droperidol may be treated with droperidol as a single therapy. By this it is meant that other agents used to treat an active episode of droperidol need not be used prior to or in conjunction with the droperidol treatment. Many patients receive various medications for prophylaxis against active migraine episodes, but such prophylactic therapy is not considered to be pretreatment of an active migraine episode, prior to droperidol treatment. Such therapy is nonspecific in that the goal is to prevent or reduce the number of occurrences of active migraine headache, but not the treatment of a specific migraine episode. The present invention will be useful as a first-line treatment of active migraine headache without the prior use of traditional migraine therapy, or as a rescue medication when other treatment has failed.

Presently, an active migraine episode may be treated with any of a number of therapies, including the following:

Simple analgesics, such as aspirin, combination analgesics as with caffeine, vasoconstrictors, narcotics, and the like.

As indicated, the use of droperidol in accordance with the present invention does not require the prior administration of such other agents for treating migraine.

The patients to whom droperidol should be administered are those that are experiencing a migraine episode or are at risk of such an episode. Such patients may be generally described as those meeting the diagnostic criteria for "migraine with aura" or "migraine without aura" as detailed in: "Classification Committee of the International Headache Society. Classification and Diagnostic Criteria For Headache Disorders, Cranial Neuroalgia and Facial Pain", *Cephalgia*, 1988, Vol. 8, Supp. 77 at pp. 19–21; or meeting the diagnostic criteria for "status migrainosus", as detailed therein at pp. 26–27.

The droperidol of use in accordance with the present invention may be administered either I.V. or I.M. The droperidol is infused as a solution in a suitable carrier such as water-for-injection, saline solution, D5W, or the like. The concentration of the droperidol in the infusion solution is not critical. Typically it will be about 2.5 mg per ml of solution. If administered intravenously, the rate of infusion also is not critical and will usually be administered by iv push in a pre-established line. Usually the droperidol will be administered intramuscularly as a bolus.

In most instances the droperidol will be administered by infusion of an initial amount of droperidol, usually 2.5 mg. If the migraine headache subsides within about 15 to 45 minutes, then no additional droperidol will be administered. If the headache has not subsided within that period of time an additional dose of 2.5 mg of droperidol may be administered. If again the headache does not subside within about 15 to about 45 minutes, a third dose of droperidol may be administered. Usually, no further administration of droperidol will be given beyond a total dosage of 7.5 mg, although doses as high as 10 mg occasionally may be required.

EXAMPLE

Patients—Patients with migrainosus (IHS code 1.6.1) or refractory migraine were recruited. Refractory migraine attacks were defined as those lasting more than 1 day but less than 3 days, and unresponsive to an adequate clinical trial of at least one of the following treatments: DHE, sumatriptan, nonsteroidal anti-inflammatory drugs, butorphanol nasal spray, or other narcotics.

All patients had physician-diagnosed migraine, with or without aura, (IHS criteria) for more than 1 year. All were established patients of the Comprehensive Headache Center at Germantown Hospital Medical Center ("GHMC"). The current headache characteristics had to fulfill the IHS migraine features, except that the headache intensity had to be moderate or severe before entering the study. Pain intensity was measured on a 4-point severity scale (0=no pain, 1=mild, 2=moderate, 3=severe). Patients were excluded if they met any of the following criteria: were younger than 15 or older than 75 years; were pregnant or possibly pregnant; had chronic daily headache, analgesic, or ergotamine rebound headache; a known history of allergy to droperidol; on current therapy with neuroleptics; had renal or hepatic impairment; or a blood pressure lower than 80/55 mm Hg. Written informed consent was obtained from all patients before entering the study.

Treatment—Patients had an IV line started and were pretreated with IV 5% dextrose water in one-fourth normal saline at a rate of 250 mL/hr. Patients then received droperidol (2.5 mg) IV push for 1 minute every 30 minutes until either a total of three doses had been given or patients became almost or completely headache-free prior to the next dose. Diphenhydramine (50 mg IV) was available on an as-needed basis for akathisia or dystonia. All treatments were given at the outpatient infusion center at GHMC.

Measurements—Vital signs (blood pressure, pulse rate) were checked before (time =0) and at 5 and 20 minutes after each dose of droperidol.

Patients were asked to judge the intensity of their headaches using the 4-point headache scale at the time the vital signs were checked (0, 5, and 20 minutes) and every 30 minutes after the first dose of droperidol was given.

The symptoms of nausea, vomiting, sensitivity to light or sound, sedation, akathisia, and dystonia were rated as present or absent every 30 minutes after the first dose of droperidol was given.

Patients were contacted by telephone 24 hours after discharge. They were asked about headache recurrence, nausea, vomiting, sedation, extrapyramidal symptoms, and the use of escape medicines. Patients were instructed before discharge to take diphenhydramine (Benadryl®) pills for extrapyramidal symptoms.

Treatment Success—Treatment was considered successful if the patient's headache was either gone or mild in intensity. The percentage of patients who were headache-free was also calculated.

Recurrence—Headache recurrence was defined as a moderate to severe headache occurring within 24 hours in patients who had mild or no headache after droperidol treatment. The percentage of recurrence of any headache within 24 hours in patients who were headache-free after treatment was also calculated.

RESULTS

Thirty-five patients (32 women, 3 men) were recruited and completed the study. Twenty-five patients had status migrainosus, while 10 had refractory migraine (Table 1). Thirty-three (94%) were on at least one headache preventive medication. None were overusing analgesics, ergotamine, or sumatriptan.

The mean dosage of droperidol was 5.6 mg in status migrainosus, and 5.6 mg in refractory migraine (Table 2). All patients improved (at least one point) after treatment (Table 2). The success rate (headache-free or mild headache) was 88% (22 of 25) in patients with status migrainosus and 100% (10 of 10) in patients with refractory migraine. The average time to headache improvement (one point below the original intensity) was 40 minutes, to mild headache—1 hour, and to no headache—1½ to 2 hours.

Only five patients (14%), four patients with status migrainosus and one patient with refractory migraine, still had nausea (n=1) or light (n=5) and sound (n=1) sensitivity after treatment.

Four patients had an asymptomatic systolic blood pressure drop $\geq 20$ mm Hg and 2 had transient asymptomatic hypertension up to 170 mm Hg. Asymptomatic tachycardia (heart rate >100 beats per minute) was found in 3 patients. No patients had respiratory difficulty during the trial. Most patients (34 of 35) experienced sedation, which lasted on average 95 minutes (range: 30 to 165) after the last dose of droperidol. During treatment, 5 patients developed akathisia and 1 had dystonia. These side effects responded to IV diphenhydramine.

Telephone follow-up was obtained on all patients 24 hours after discharge (Table 3). The headache recurrence rate was 23% in patients with status migrainosus and 10% in patients with refractory migraine. In all, 72% of status migrainosus and 90% of refractory migraine patients remained headache-free or had mild headache. Nine (32%) of 28 patients who were originally headache-free had some recurrent headache. The average time for headache recurrence in these 9 patients was 8±5 (4 to 18) hours. Five patients (20%) with status migrainosus and 1 patient (10%) with refractory migraine took escape medicines for headache relief within 24 hours. Six patients still had nausea, 1 had vomiting, 6 had sensitivity to light, and 4 sensitivity to sound. Twenty-one patients (60%) had some degree of drowsiness. Nineteen patients (54%) had akathisia and 2 had dystonic reactions. Seventeen of these 19 patients took diphenhydramine tablets for symptomatic relief. The occurrence of sedation ($X^2$=0.14, df=2, P=0.93) or extrapyramidal symptoms ($X^2$=1.62, df=2, P=0.44) was not dose related.

In order to evaluate the relationship between the treatment results and headache duration, the status migrainosus patients were divided into two groups by their current headache duration (<7 and $\geq 7$ days) (Table 4). The success rates decreased as the duration of current headache increased, especially in the status migrainosus patients with duration $\geq 7$ days. The trend remained for the follow-up results after 24 hours.

This study demonstrated the efficacy of droperidol in the treatment of status migrainosus and refractory migraine attacks. The success rate (headache-free or mild headache) was 88% of status migrainosus patients and 100% of refractory migraine patients. About 72% of status migrainosus patients and 100% of refractory migraine patients became headache-free. Most patients (72% of patients with status migrainosus and 90% of patients with refractory migraine) continued to do well after 24 hours; they were either free of headache or had a mild headache. The recurrence rate in the patients with status migrainosus (23%) was higher than the patients with refractory migraine (10%). In status migrainosus patients, the patients with duration shorter than 1 week did better than patients with duration longer than 1 week. This suggests that the duration of the headache is of prognostic significance and that early aggressive treatment may be more beneficial.

TABLE 1

Patient Characteristics

| Feature | Status Migrainosus Group (n = 25) | Refractory Migraine Group (n = 10) | Total (N = 35) |
|---|---|---|---|
| Age, y* | 42 ± 9 (16–58) | 46 ± 13 (23–70) | 43 ± 10 (16–70) |
| Ratio of men to women | 2:23 | 1:9 | 3:32 |
| History of migraine, y* | 13 ± 12 (1–48) | 20 ± 17 (2–42) | 15 ± 14 (1–48) |
| Prior migraine diagnosis, with/without aura | 8/17 | 3/7 | 11/24 |
| Current migraine diagnosis, with/without aura | 4/21 | 2/8 | 6/29 |
| Preventive medication | 24 | 9 | 33 |
| Duration of current headache, d* | 7.0 ± 3.5 (3–13) | 1.4 ± 0.5 (1–2) | 5.4 ± 3.9 (1–13) |
| Headache intensity, moderate/severe | 10/15 | 4/6 | 14/21 |
| Nausea | 19 | 9 | 28 |
| Photophobia | 12 | 7 | 19 |
| Phonophobia | 13 | 7 | 20 |

*Values given as mean ± SD (range). All other values given as number of patients.

TABLE 2

Results of Droperidol Treatment

| | Status Migrainosus Group (n = 25) | Refractory Migraine Group (n = 10) | Total (N = 35) |
|---|---|---|---|
| Droperidol use, No. | | | |
| One dose (2.5 mg) | 5 | 2 | 7 |
| Two doses (5 mg) | 9 | 3 | 12 |
| Three doses (7.5 mg) | 11 | 5 | 16 |
| Success rate, No. (%) | | | |
| Headache ≤ 1 | 22 (88) | 10 (100) | 32 (91) |
| Headache = 0 | 18 (72) | 10 (100) | 28 (80) |
| Mean time to improvement, min (range) | | | |
| Some improvement* | 35 (5–115), n = 25 | 40 (5–90), n = 10 | 40 (5–120), n = 35 |
| Mild headache | 60 (5–240), n = 22 | 65 (20–120), n = 10 | 60 (5–240), n = 32 |
| Headache-free | 90 (30–150), n = 18 | 125 (80–210), n = 10 | 105 (5–210), n = 28 |
| Residual associated symptoms, No. | | | |
| Nausea | 1 | 0 | 1 |
| Photophobia | 4 | 1 | 5 |
| Phonophobia | 1 | 0 | 1 |

*Headache decreased one point below the original intensity.

TABLE 3

Results of Follow-up 24 Hours Postdischarge

| | Status Migrainosus Group (n = 25) No. (%) of Patients | Refractory Migraine Group (n = 10) No. (%) of Patients | Total (N = 35) No. (%) of Patients |
|---|---|---|---|
| Headache intensity | | | |
| Headache 2–3 | 7 (28) | 1 (10) | 8 (23) |
| Headache 1 | 5 (20) | 2 (20) | 7 (20) |
| Headache 0 | 13 (52) | 7 (70) | 20 (57) |
| Headache Recurrence | | | |
| Headache 0.1 → 2.3 | 5/22 (23) | 1/10 (10) | 6/32 (19) |
| Headache 0 → >0 | 6/18 (33) | 3/10 (30) | 9/28 (32) |
| Side effects | | | |
| Sedation | 13 (52) | 7 (70) | 21 (60) |
| Akathisia | 16 (64) | 3 (30) | 19 (54) |

TABLE 3-continued

Results of Follow-up 24 Hours Postdischarge

| | Status Migrainosus Group (n = 25) No. (%) of Patients) | Refractory Migraine Group (n = 10) No. (%) of Patients | Total (N = 35) No. (%) of Patients |
|---|---|---|---|
| Dystonia | 2 (8) | 0 | 2 (6) |
| Benadryl ® | 16/16 (100) | 1/3 (33) | 17/19 (89) |
| Escape medicine | 5 (20) | 1 (10) | 6 (17) |

TABLE 4

Results of Treatment With Droperidol Among Groups With Different Duration of Current Headaches

| | No. (%) of Patients With Refractory Migraine 1 to 3 Days n = 10 | No. (%) of Patients With Status Migrainosus 3 to 7 Days n = 11 | No. (%) of Patients With Status Migrainosus > 7 Days n = 14 |
|---|---|---|---|
| Success rate | | | |
| Headache ≦ 1 | 10 (100) | 11 (100) | 11 (79) |
| Headache 0 | 10 (100) | 10 (91) | 8 (57) |
| Success rate after 24 hours | | | |
| Headache ≦ 1 | 9 (90) | 8 (73) | 10 (71) |
| Headache 0 | 7 (70) | 7 (64) | 6 (43) |

What is claimed is:

1. A method of treating a migraine episode in a patient comprising administering droperidol, either intravenously or intramuscularly, to a patient that is experiencing a migraine episode, in an amount that is effective to treat symptoms of migraine.

2. The method of claim 1 in which from about 2.5 to about 10 mg of droperidol is administered to the patient.

3. The method of claim 2 in which the administration is intravenous.

4. The method of claim 2 in which the administration is intramuscular.

5. The method of claim 3 in which the patient failed to respond to other migraine therapy prior to receiving droperidol.

6. The method of claim 4 in which the patient failed to respond to other migraine therapy prior to receiving droperidol.

* * * * *